(12) United States Patent
Santini et al.

(10) Patent No.: US 10,124,082 B2
(45) Date of Patent: Nov. 13, 2018

(54) FRAGRANCE DELIVERY DEVICE, SYSTEM, AND METHOD

(71) Applicant: TAKASAGO INTERNATIONAL CORP. (USA), Rockleigh, NJ (US)

(72) Inventors: Thomas F. Santini, Doylestown, PA (US); Anthony R. Budraitis, Lambertville, NJ (US)

(73) Assignee: TAKASAGO INTERNATIONAL CORPORATION (USA), Rockleigh, NJ (US)

( * ) Notice: Subject to any disclaimer, the term of this patent is extended or adjusted under 35 U.S.C. 154(b) by 0 days.

(21) Appl. No.: 14/898,347

(22) PCT Filed: Jun. 30, 2014

(86) PCT No.: PCT/US2014/044949
§ 371 (c)(1),
(2) Date: Dec. 14, 2015

(87) PCT Pub. No.: WO2015/002900
PCT Pub. Date: Jan. 8, 2015

(65) Prior Publication Data
US 2016/0144063 A1    May 26, 2016

Related U.S. Application Data (60) Provisional application No. 61/841,797, filed on Jul. 1, 2013.

(51) Int. Cl.
*A61L 9/12*    (2006.01)
*A61L 9/04*    (2006.01)
*A01M 1/20*    (2006.01)

(52) U.S. Cl.
CPC ........... *A61L 9/127* (2013.01); *A01M 1/2044* (2013.01); *A61L 9/04* (2013.01); *A61L 9/12* (2013.01)

(58) Field of Classification Search
CPC ...... A61L 9/12; A61L 9/127; A61L 2209/133; A61L 9/03; A61L 9/037; A01M 1/2044; A41G 1/006
(Continued)

(56) References Cited

U.S. PATENT DOCUMENTS 2,586,179 A * 2/1952 Rooch ........................ A61L 9/12
239/42
3,587,968 A * 6/1971 Hennart .................... A61L 9/12
239/309
(Continued)

FOREIGN PATENT DOCUMENTS

EP      2 545 942 A1    1/2013
WO   WO 2013/043581 A1   3/2013

OTHER PUBLICATIONS

U.S. Appl. No. 14/898,366 (US 2016/0144064), filed Dec. 14, 2015 (May 26, 2016).
(Continued)

*Primary Examiner* — Alexander Valvis
(74) *Attorney, Agent, or Firm* — Baker Botts L.L.P.

(57) ABSTRACT

A fragrance delivery device, system and method is provided, comprising a housing including a rupture device and an absorbent member receivable in the housing. The system further includes a cartridge insertable within the housing and containing a fragrance medium therein. The rupture device of the housing is engageable with the cartridge to release the fragrance medium from the cartridge into the housing. The absorbent member absorbs the fragrance medium and permeates a fragrance from the fragrance medium to an external environment.

21 Claims, 7 Drawing Sheets

(58) Field of Classification Search
USPC .............................. 239/6, 34, 43, 44, 57, 56
See application file for complete search history.

(56) References Cited

U.S. PATENT DOCUMENTS

| | | | |
|---|---|---|---|
| 4,161,284 A | | 7/1979 | Rattan |
| 4,247,042 A | * | 1/1981 | Schimanski ........ A01M 1/2044 239/43 |
| 4,323,193 A | | 4/1982 | Compton et al. |
| 4,505,429 A | * | 3/1985 | Mandon ................ A61L 9/12 239/56 |
| 4,526,320 A | * | 7/1985 | von Philipp ........ A01M 1/2044 239/34 |
| 4,630,775 A | * | 12/1986 | Mandon .............. A01M 1/2044 239/56 |
| 4,995,555 A | | 2/1991 | Woodruff |
| 5,749,519 A | | 5/1998 | Miller |
| 6,553,712 B1 | * | 4/2003 | Majerowski ........ A01M 1/2011 239/44 |
| 6,610,254 B1 | | 8/2003 | Furner et al. |
| 6,713,024 B1 | | 3/2004 | Arnell et al. |
| 6,790,408 B2 | | 9/2004 | Whitby et al. |
| 7,093,773 B2 | | 8/2006 | Kuiper |
| 7,407,114 B2 | | 8/2008 | Carter |
| 7,896,256 B2 | | 3/2011 | Robbinis-Sullivan et al. |
| 8,191,796 B2 | | 6/2012 | Lammert et al. |
| 2010/0314461 A1 | | 12/2010 | Gruenbacher et al. |
| 2011/0079658 A1 | | 4/2011 | Santini et al. |
| 2012/0312893 A1 | | 12/2012 | Santini et al. |

OTHER PUBLICATIONS

International Search Report dated Oct. 30, 2014 in International Application No. PCT/US2014/044949.
International Search Report dated Oct. 30, 2014 in International Application No. PCT/US2014/044956.
Supplementary European Search Report dated Jan. 4, 2017 in Application No. EP 14819425.
Supplementary European Search Report dated Jan. 4, 2017 in Application No. EP 14819785.
U.S. Appl. No. 14/898,366, Aug. 16, 2017 Final Office Action.
U.S. Appl. No. 14/898,366, Mar. 3, 2017 Non-Final Office Action.

* cited by examiner

FRAGRANCE DELIVERY DEVICE, SYSTEM, AND METHOD

CROSS-REFERENCE TO RELATED APPLICATIONS

The present application is a U.S. National Stage Patent Application under 35 U.S.C. § 371 of International Application No. PCT/US2014/044949, filed on Jun. 30, 2014, which claims the benefit of U.S. Provisional Application No. 61/841,797 filed on Jul. 1, 2013, the contents of each of which are incorporated herein by reference in their entireties.

BACKGROUND OF THE DISCLOSED SUBJECT MATTER

Field of the Disclosed Subject Matter

The disclosed subject matter relates to a fragrance delivery device, system, and method of use.

Description of the Related Art

A number of methods exist for dispensing a volatile fragrance material into the air in order to create a pleasant indoor fragrance experience and/or for counteracting or neutralizing offensive odors. Previous methods utilizing vessels made from porous materials such as ceramic, have been used as a means to provide a fragrance environment. Typically, these products are offered with a pre-measured amount of fragrance, which is simply poured into the vessel in order to initiate activation. Migration of the fluid fragrance into the absorbent vessel completes the process. A glazing on a portion of the vessel protects surfaces from unwanted exposure to the fragrance.

Other conventional devices include absorbent structures saturated with fragrance oil, which are sealed in a vapor impermeable enclosure. The structures are activated by removing the article from the enclosure and allowing the structure to be exposed in a confined space to create a fragrance awareness. The absorbent structures used for such application include paper, wood, ceramic, nonwovens, felted fabrics, and polymeric substrates, which can be infused with fragrance, such as ethylene-vinyl acetate copolymer, polyethylene, polypropylene, polyvinyl chloride, and assorted closed and open celled foams, to include those based on polyurethane, polyether and polyester chemistries, and the like.

In contrast to the release of fragrance from an inert substrate, other forms of products in this category rely upon the co-evaporation of fragrance along with an inert carrier. The most common of these formats is represented by water based gels, in which the water and fragrance co-evaporate resulting in the ever diminishing size of the gel, as the volatile components of the formula release, leaving the gel matrix to slowly collapse onto itself.

Another format in which co-evaporation is an integral component is found in liquid wicks. Again, the release of fragrance, water, and volatile solvents, from some form of polymeric or cellulosic wick in liquid contact with the reservoir, creates an evaporative release of actives to provide an indoor odor awareness.

One drawback of the conventional devices, such as those noted above, is that the stability and the integrity of the fragrance diminishes over the projected shelf life of the device even, when the device remains unopened and unexposed to an external environment. Furthermore, such conventional devices experience deleterious interactions between the fragrance materials and outside interactions such as oxygen, heat, and ultraviolent light. Fragrances made in anticipation of these deleterious interactions frequently limit the range of the raw materials available for use in the fragrance. Therefore, raw materials that are highly fugitive or aggressive against packaging components, or which might be inherently unstable over a prolonged period of time on a shelf, are selectively omitted from use in these fragrance formulations. Aggressive materials such as citrus oils, terpenes, acetates, and aldehydes are thereby frequently avoided, as these materials have a high potential to negatively interact with the packaging materials. These anticipated limitations restrict olfactory experiences, which can be more fulfilling to consumers had the raw material options not been restricted out of concern for such deleterious packaging issues and fragrance stability concerns.

Furthermore, frequently hostile processing conditions are used for a number of product forms that impact fragrances in a negative way during the course of product manufacturing. For example, incorporation of fragrances such as into polymeric substrates, requires processing conditions in excess of approximately 300 degrees Fahrenheit, whereas hydrocolloid based gels require processing at approximately 85 degrees Fahrenheit.

It is known that fragrance products held at elevated temperatures, such as during the time allocated to prepare and fill the products into suitable packaging, frequently require several hours on a production filling line. The processing time at such elevated temperatures can create a hostile environment for the fragrance. Furthermore, such processing times can create a negative impact on the materials in the fragrance, which are more fugitive. Such materials often are driven off into the external environment and never manage to be incorporated into the fragrance product for which they were intended and thus never reach the consumer.

Thus, there remains a continued need for an improved fragrance delivery system, a fragrance delivery device, and method of use. The presently disclosed subject matter satisfies these and other needs.

SUMMARY OF THE DISCLOSED SUBJECT MATTER

The purpose and advantages of the disclosed subject matter will be set forth in and are apparent from the description that follows, as well as will be learned by practice of the disclosed subject matter. Additional advantages of the disclosed subject matter will be realized and attained by the devices particularly pointed out in the written description and claims hereof, as well as from the appended drawings.

To achieve these and other advantages in accordance with the purpose of the disclosed subject matter, as embodied and broadly described, the disclosed subject matter includes a fragrance delivery system, comprising a housing including a rupture device and an absorbent member receivable in the housing. The system further includes a cartridge insertable within the housing and containing a fragrance medium therein. The rupture device of the housing is engageable with the cartridge to release the fragrance medium from the cartridge into the housing. The absorbent member absorbs the fragrance medium and permeates a fragrance from the fragrance medium to an external environment.

In accordance with another aspect of the disclosed subject matter, a fragrance delivery device is provided, comprising: a housing including a top surface, at least one sidewall coupled to the top surface, and a base member including a rupture device, wherein the top surface defines an aperture therein. The device further includes an absorbent member disposed within the housing, wherein the base member supports the absorbent member and a cartridge insertable within the aperture of the top surface and containing a fragrance medium therein. The top surface is deflectable towards the base member to engage a bottom of the cartridge with the rupture device to release the fragrance medium from the cartridge into the base member and wherein the absorbent member absorbs the fragrance medium and permeates a fragrance from the fragrance medium to an external environment.

In accordance with another aspect of the disclosed subject matter, a method of operating a fragrance delivery system is provided, comprising providing a fragrance delivery device including a housing including a rupture device, and an absorbent member receivable in the housing. The method further includes inserting a cartridge within the housing, wherein the cartridge contains a fragrance medium therein. The method further includes engaging the cartridge with the rupture device of the housing to release the fragrance medium from the cartridge into the housing, wherein the absorbent member absorbs the fragrance medium and permeates a fragrance from the fragrance medium to an external environment.

It is to be understood that both the foregoing general description and the following detailed description and drawings are examples and are provided for purpose of illustration and not intended to limit the scope of the disclosed subject matter in any manner.

The accompanying drawings, which are incorporated in and constitute part of this specification, are included to illustrate and provide a further understanding of the devices of the disclosed subject matter. Together with the description, the drawings serve to explain the principles of the disclosed subject matter.

BRIEF DESCRIPTION OF THE DRAWINGS

The subject matter of the application will be more readily understood from the following detailed description when read in conjunction with the accompanying drawings, in which.

DETAILED DESCRIPTION

Reference will now be made in detail to embodiments of the disclosed subject matter, an example of which is illustrated in the accompanying drawings. The disclosed subject matter will be described in conjunction with the detailed description of the system.

In accordance with one aspect of the disclosed subject matter, a fragrance delivery device and system is provided, comprising a housing including a rupture device and an absorbent member receivable in the housing. The system further includes a cartridge insertable within the housing and containing a fragrance medium therein. The rupture device of the housing is engageable with the cartridge to release the fragrance medium from the cartridge into the housing. The absorbent member absorbs the fragrance medium and permeates a fragrance from the fragrance medium to an external environment.

A method of operating the fragrance delivery device and system described above is also disclosed. The details of the method of operation will be described in detail in conjunction with the features of the fragrance delivery device.

Figure 1:
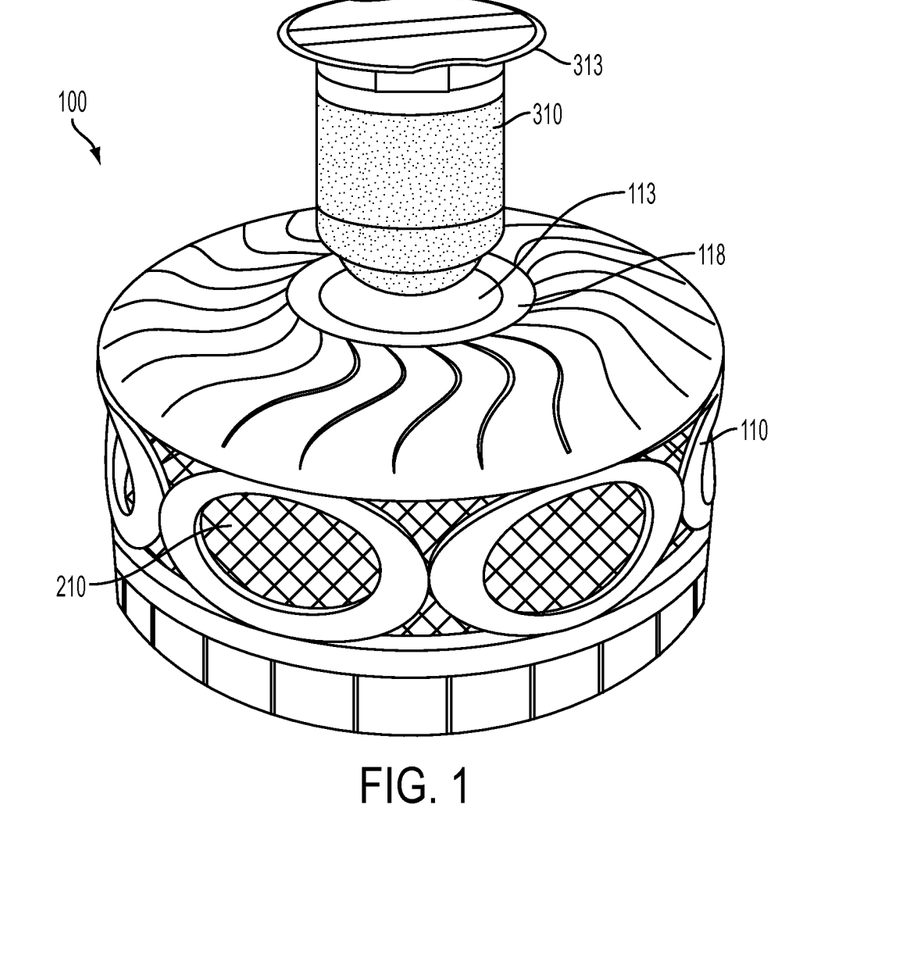
FIG. 1 is a perspective view of a fragrance delivery device and system with a cartridge external to a housing, according to the disclosed subject matter.
Figure 2:
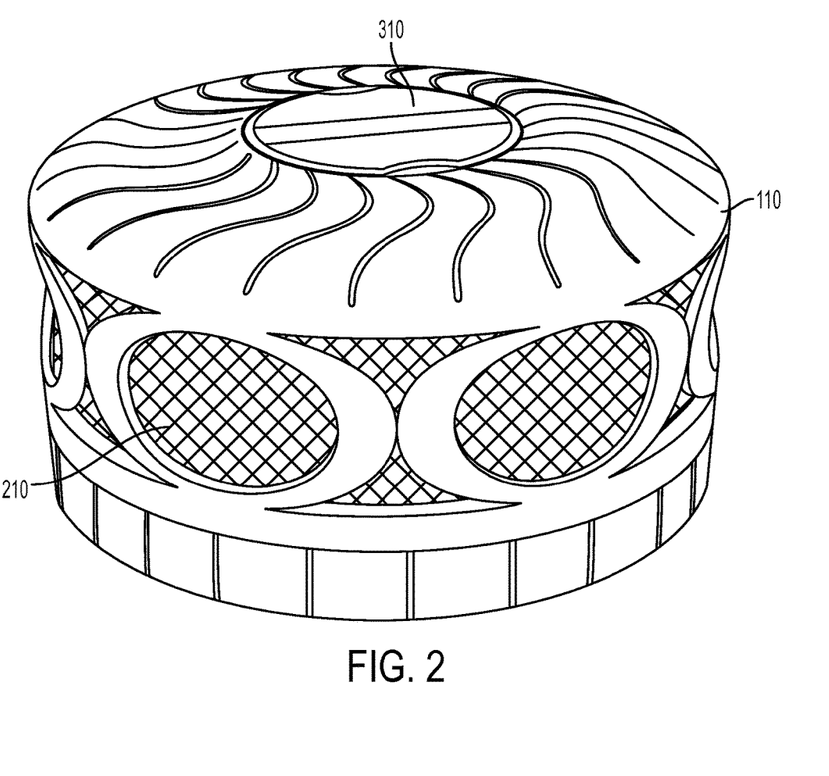
FIG. 2 is a perspective view of the fragrance delivery device of FIG. 1 with the cartridge engaged with the housing, according to the disclosed subject matter.

Solely for purposes of illustration, an exemplary embodiment of a fragrance delivery device, system, and method of use, is shown schematically in FIG. 1. The examples herein are not intended to limit the scope of the disclosed subject matter in any manner. The fragrance delivery device 100 of FIG. 1 includes a housing 110, an absorbent member 210, and a cartridge 310 containing a fragrance medium. The cartridge 310 is receivable within the housing 110. In FIG. 1, the cartridge 310 is external to the housing 110. In FIG. 2, the cartridge 310 is engaged with the housing 110.

Figure 3:
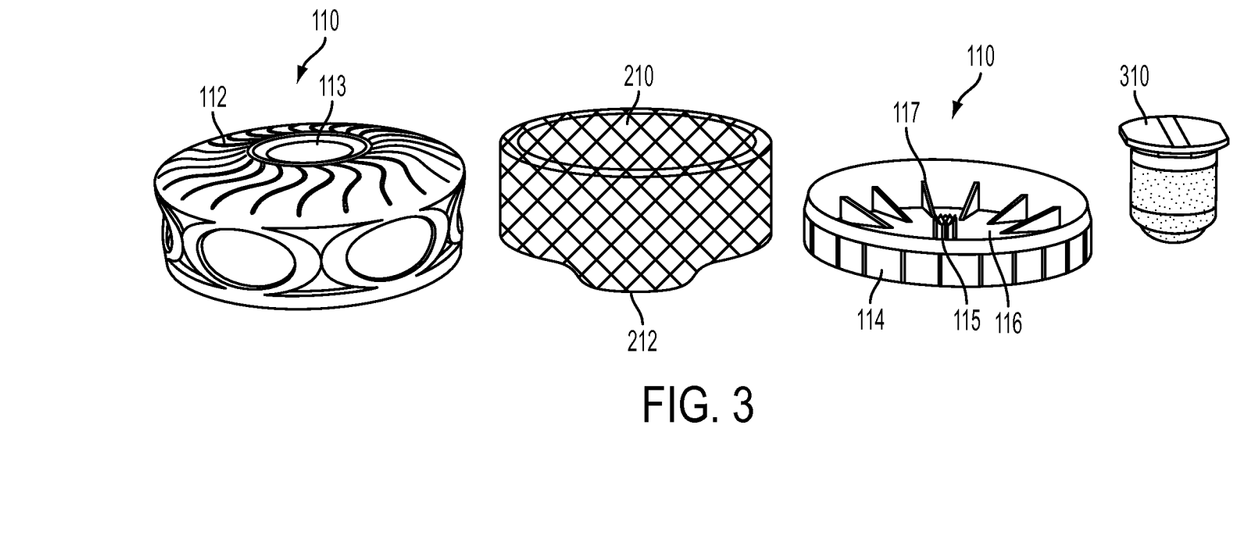
FIG. 3 is an exploded view of the fragrance delivery device of FIG. 1, according to the disclosed subject matter.

FIG. 3 depicts an exploded view of the fragrance delivery system and device of FIG. 1. As depicted, the housing 110 includes a top member 112 and a base member 114. The housing can additionally include a lid member (not shown), as desired. When the fragrance delivery device is assembled as a unit, the top member 112 is coupled to the base member 114. In the embodiment of FIG. 3, the top member 112 and the base member 114 can be coupled together such that the top member 112 is friction fitted together with the base member 114 for the purposes of a unitary engagement. However, the top member 112 and the base member 114 can be coupled together in a plurality of suitable ways as known in the art such as, but not limited to, a snap fit or a latching mechanism or a threaded union.

The top member 112 can include a top surface coupled to at least one sidewall, as shown in FIG. 3. The top member 112 defines at least one aperture 113. The aperture 113 receives and houses the cartridge 310. As depicted in FIG. 1, the aperture 113 can include a lip portion 118 that corresponds with a flange 313 of the cartridge 310. The lip portion 118 is indented such that the top face of the cartridge is flush with the top face of the top member 112 when engaged. Other embodiments of the disclosed subject matter contemplate the top member having one or more apertures to receive one or more cartridges, respectively. For example, in the embodiment of FIG. 4 and FIG. 5, the top member 112 defines two apertures 113 which each receive cartridges 310, respectively.

The top member 112 can further include a plurality of slits and recesses to promote permeation of fragrance to an external environment, as further discussed herein. The slits and apertures can increase the flexibility of the housing to allow the top member to deform or depress, such as for example, approximately 0.2 inches to approximately 0.45 inches toward the base member upon application of a downward force. The top can deform when sufficient force is applied between approximately 7 to approximately 15% of the diameter of the top member. Any suitable downward force is contemplated herein such as the force applied if a finger or a palm of a hand were used to deflect the top member or cartridge therein downward. As discussed further herein, the downward force causes the cartridge to engage a rupture device and cause an opening in the bottom of the cartridge, allowing the fluid contents of the cartridge to empty.

Figure 4:
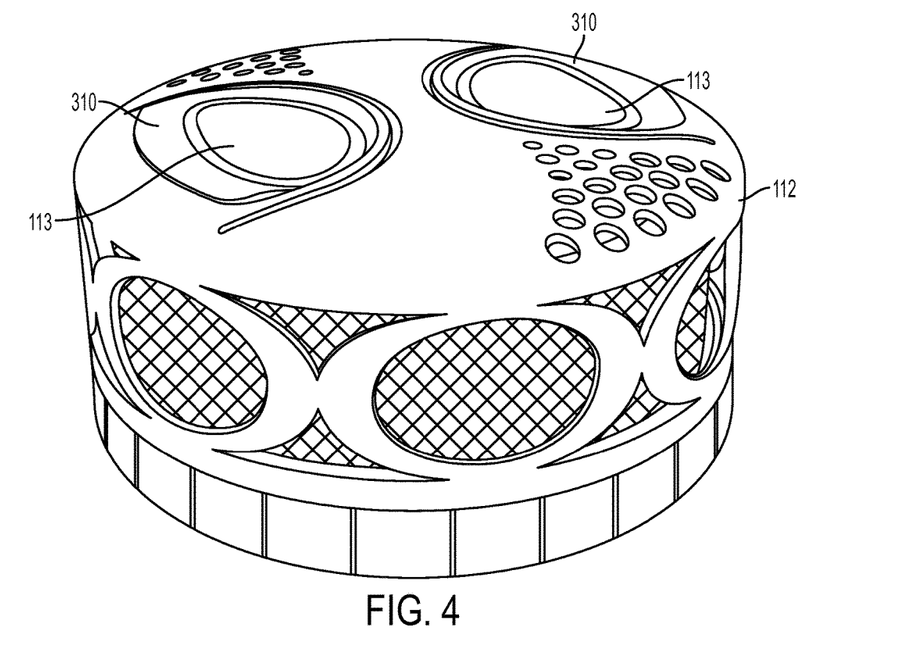
FIG. 4 is another embodiment of the fragrance delivery system and device, according to the disclosed subject matter.
Figure 5:
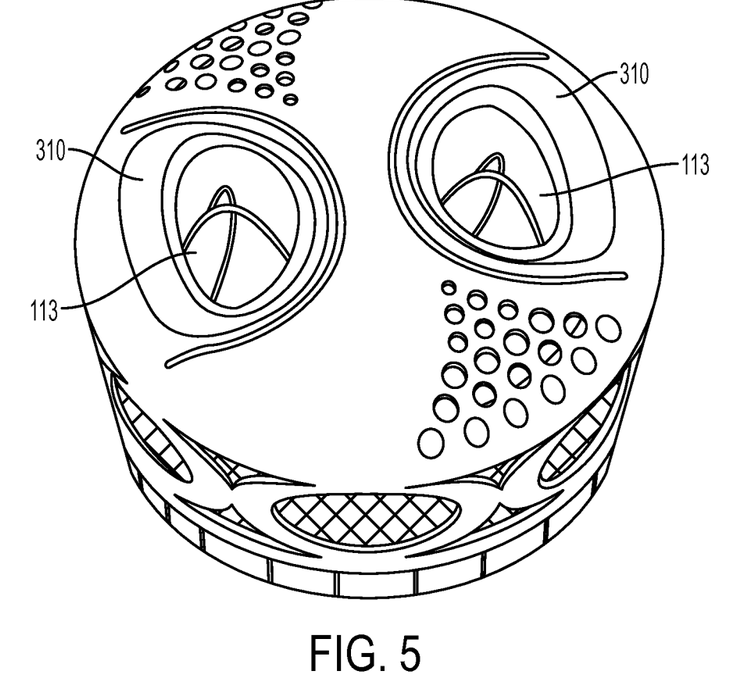
FIG. 5 is a top perspective view of the fragrance delivery device of FIG. 4, according to the disclosed subject matter.

In another embodiment, the slits and openings in the top member can be used to enhance flexibility or remain otherwise decorative. Turning back to the embodiment of FIGS. 1-3, the top member 112 includes a pattern of slits on the top surface. The pattern in this embodiment is an ordered pattern in which the slits are equally spaced from each other. In this embodiment, the single aperture 113 together with the pattern of slits effectuates a sun appearance on the top surface of the top member 112. Other designs and configurations of apertures and slits are further contemplated herein. The slits and apertures can further be arranged randomly or can be arranged to effectuate other designs. Any design that allows for slits or openings to allow the scent of the fragrance to disseminate to an external environment is contemplated herein. As depicted in the embodiment of FIG. 4-5, the top surface of the top member 112 includes a pattern of circular openings and the apertures 113 for the cartridges 310 are each accompanied by a long slit surrounding respective aperture 113.

The sidewall of the top member 112 can be integral with the top surface, as depicted in FIGS. 1-3. Alternatively, the sidewall can be a separate member as further described with respect to FIG. 3B herein. The sidewall can include recesses and slits in the sidewall thereof. As depicted in FIGS. 1-3, the sidewall defines a pattern of elliptical shapes and openings or recesses. The configuration of the sidewall can further promote permeation of fragrance to an external environment. In other embodiments, the base member 114 can include the sidewall (not shown) with the aperture and slits instead of the top member 112. In such embodiments, a top member can be coupled to the sidewall of the base member in any suitable manner.

The base member 114 can include a rupture device 115 such as a piercing lance, as shown in FIG. 3. The rupture device 115 engages or pierces the bottom of the cartridge 310 to release a fragrance medium contained within the cartridge. The top of the rupture device is configured to pierce and allow the contents of the cartridge to empty. The rupture device does not act as a plug. As depicted in FIG. 3, the rupture device 115 is arranged in the approximate center of the base member 114. However, the rupture device 115 can be arranged at any suitable position in the base member 114 which corresponds to the position of the cartridge to be engaged. For example, in the embodiment of FIGS. 4-5, the top member 112 includes two apertures 113 positioned approximately in equal locations with respect to a center of the housing 110 which receive respective cartridges 310. A corresponding rupture device (not shown) of the base member 114 of this embodiment is arranged at an approximate location corresponding to one of the recesses (i.e., off-center). The embodiment of FIGS. 4-5 allow for one cartridge to be engaged with the rupture device 115 at a time while the second cartridge is in reserve. Once the first cartridge is used, the top member 112 can be rotated or adjusted with respect to the base member 114 such that the second cartridge can be engaged with the rupture device 115 at a desired time. Other embodiments of the disclosed subject matter contemplate a base member including more than one rupture device. Further embodiments include the rupture device disposed at any suitable location of the device, With any embodiment, the aperture 113 can additionally include a cap (not shown) to be engaged with the aperture when a cartridge is not present.

In another embodiment, the top member 112 includes at least one aperture having an open framed cup holder structure for holding the cartridge 310. In this embodiment, the cup holder can include the rupture device at the base of the cup holder instead of the rupture device being a part of the base member 114. This can allow the fragrance medium to drain from the cartridge 310 directly into the base member 114.

Figure 3A:
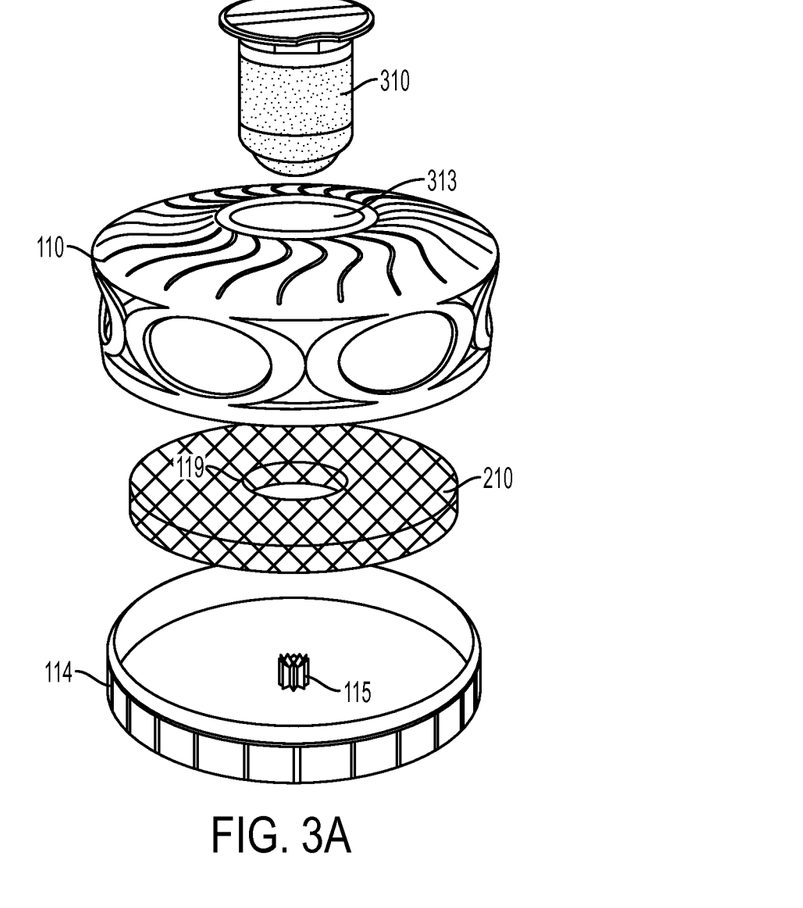
FIG. 3A is an exploded view of another embodiment of a fragrance delivery device, according to the disclosed subject matter.
Figure 3B:
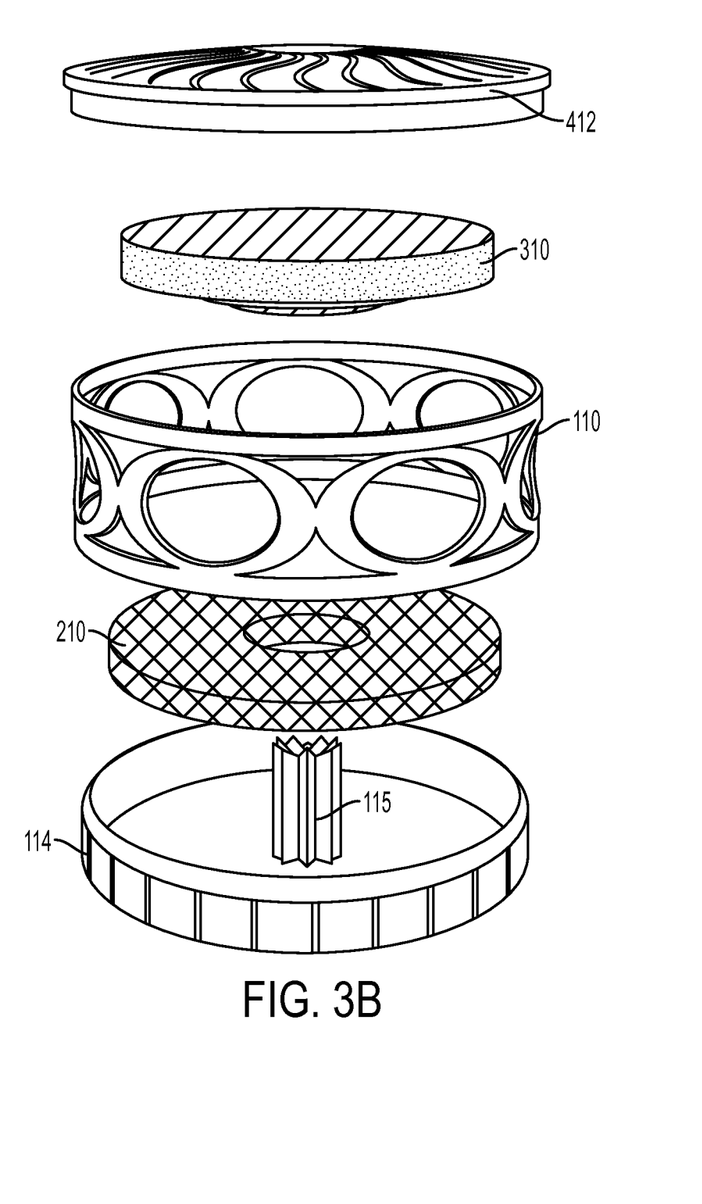
FIG. 3B is an exploded view of a further embodiment of a fragrance delivery device having a depressible lid, according to the disclosed subject matter.

The rupture device can have any suitable dimension and configuration suitable to engage a cartridge. For example, the rupture device can have a height dimension ranging from approximately 0.3 inches to approximately 1.5 inches. As shown in FIG. 3, the rupture device 115 is approximately 0.3 inches, whereas the rupture device in FIG. 3B is approximately 0.7 inches.

In at least the embodiment of FIGS. 1-3, the base member 114 further includes a reservoir basin 116 in which fragrance medium released from the cartridge 310 can be temporarily contained. The reservoir basin 116 is in a convex configuration and channels the fragrance medium away from a center of the base towards a contact surface of the absorbent member 210.

The base member 114 can further include supports 117. The supports 117 can engage with the absorbent member 210 to keep the absorbent member 210 in a desired position. In the embodiment of FIG. 3, the supports 117 are spaced from the sidewall of the base member 114 to create a channel. The channel can receive the absorbent member 210 such that the supports 117 engage the absorbent member 210 on an interior surface of the absorbent member 210 and the support member is disposed between the sidewall and supports 117. The supports 117 can be any suitable shape or size. As depicted, the supports 117 are triangular in configuration and spaced radially with respect to a center of the housing 110. The supports 117 can further include just one support or can include a plurality of supports 117 as shown. The supports 117 can furthermore be spaced in a pattern or randomly.

The housing 110 contains the absorbent member 210, as indicated above. In the embodiment of FIGS. 1-3, the absorbent member 210 is depicted as a ring or cylindrical structure, but any suitable shape is contemplated herein. The embodiment of FIGS. 3A and 3B depicts the absorbent member 210 as a disc structure, and is further described herein. The absorbent member 210 absorbs the fragrance medium released from the cartridge 310. The absorbent member 210 has an emanating surface to emit the fragrance medium absorbed therein to an external environment. The absorbent member 210 can absorb the fragrance medium in any desired amount of time. In some embodiments, the fragrance medium is mostly absorbed by the absorbent member 210, but a certain desired amount of the medium stays within the base to allow the absorbent member 210 to be replenished. In such embodiments, the base member of fragrance delivery device can additionally function as a wicking air freshener. Furthermore, the excess medium can reside in the base member where it can replenish the absorbent member as space becomes free in the absorbent member to absorb additional medium, due to the loss of the volatile components of the fragrance medium emanating from the absorbent member over a period of time. In another embodiment, the absorbent member 210 absorbs approximately 8 grams of the fragrance medium within approximately 90 minutes such that no fragrance medium remains in the basin 116.

Depending on the size of the housing 110 or absorbent member 210 and the amount of fragrance used within the unit, the absorption time of the absorbent member 210 can vary. In an embodiment, the absorbent member absorbs approximately 1 gram of fragrance medium per approximately 5 minutes to approximately 10 minutes. In another embodiment, the absorbent member 210 absorbs approximately 1 gram of fragrance medium per approximately 7.5 minutes. The absorbent time is a function of both the nature of the composition being absorbed and the geometry of the absorbent member in contact with the fluid medium. The absorbent member can be sized to provide for a functional life and odor intensity such that the fragrance emanating from the absorbent members creates an indoor odor awareness that meets consumer expectations for these critical performance attributes.

The absorbent member 210 diffuses the fragrance medium to an external environment for a desired time frame. In one embodiment, the absorbent member diffuses the fragrance medium to an external environment for at least 28 days or approximately four weeks. In other embodiments, the absorbent member diffuses the fragrance medium to an external environment for approximately eight weeks.

The absorbent member 210 can be any desired color or fabricated in such a way as to have a pattern or texture impressed upon the absorbent member during manufacturing. However, in one embodiment, the absorbent member 210 is a neutral color such as white or tan. The absorbent member 210 can have chameleon-esque characteristics, in which the absorbent member 210 can change color depending on the color of the fragrance medium absorbed. For example, FIG. 1 depicts the cartridge 310 containing a tinted or colored fragrance medium having a "citrus breeze" fragrance and colorant whereas the absorbent member 210 is depicted in an initial white color. As depicted in FIG. 2, the cartridge 310 has been inserted in the recess and engaged with the rupture device 115. In FIG. 2, the absorbent member 210 has had time to absorb the fragrance medium such that the absorbent member 210 has changed color from white to the tinted color of the fragrance medium. The absorbent member 210 can change to any color depending on the color of the fragrance medium. All colors, textures, and contrast of fragrance mediums are contemplated herein. The color of the fragrance can complement the configuration of the housing. For example, the housing of FIG. 1-3 is in the shape or likeness of a sun in which the aperture 113 with the cartridge 210 is the sun and the slits of the top member 112 resemble rays. The housing 110 can be light blue in color, representing the sky, with the fragrance medium and the cartridge 310 being a yellow color to represent the sun. Once the fragrance medium is absorbed, the absorbent member 210 can further change to the yellow color. In other embodiments, the housing 110 and the fragrance medium can be the same color for uniformity.

The absorbent member 210 can contact the reservoir basin 116 along the bottom surface of the absorbent member 210 to allow the absorbent member to absorb fragrance medium contained in the reservoir basin 116 via capillary transference. Once absorbed, the fragrance medium is evenly distributed throughout the absorbent member 210. In some embodiments, the absorbent member 210 has a continuous surface that contacts the reservoir basin 116. In other embodiments and as depicted in FIG. 3, the absorbent member 210 has discrete contact sections 212 with the reservoir basin 116. The discrete contact sections 212 can correspond to holding sections defined in the base member 114 (not shown) for mating and securing the absorbent member 210 with the housing 110. Alternatively or in addition thereto, the discrete contact sections 212 can control the rate of absorption of the fragrance medium.

FIG. 3A depicts an exploded view of a further embodiment of the disclosed subject matter. In this embodiment, the absorbent member 210 is embodied as a planar disc structure and has a greater contact surface area with the base member than the embodiment of FIGS. 1-3. The absorbent member 210 defines an aperture 119 that has a center positioned approximately concentric with a center of the rupture device 115. As such, the aperture 119 enables the rupture device 115 to be inserted therein to engage a cartridge 310. In this embodiment of FIG. 3A, the top surface of the housing includes an open patterned sidewall and the cartridge 310 is received within the aperture 313 of the top member. Although the base member of this embodiment does not depict supports, the base member can have supports or depressions therein that complement the absorbent member for securement of the absorbent member with the base member. The base member 114, housing 110, absorbent member 210, cartridge 310, and lid member 412 can be coupled together to form a unitary device.

FIG. 3B depicts an exploded view of another embodiment of the disclosed subject matter. In this embodiment, the cartridge 310 is not engaged with a top member via an aperture therein. Rather, the cartridge resided beneath the underside of a compressible lid member 412 and supports itself as the bottom of the cartridge 310 rests on or immediately above the rupture device 115. The compressible lid member 412 is engageable and interfaces with the sidewall of the housing 110 such that the lid member 412 is disposed above the absorbent member 210. Accordingly, the lid member 412 has a range of flexibility to allow the lid member to flex without compromising the structural integrity of the lid member. In this embodiment, the rupture device 115 is disposed at a distance from the cartridge 310 affixed to the lid member 412 in its initial position. However, upon force or pressure applied to the lid member 412, the cartridge 310 moves toward and engages with the rupture device 115 in a second position. In another embodiment, the cartridge 310 is positioned above and engages with the absorbent member 210 in a stacked relationship instead of being coupled directly to the lid member 412.

Mild pressure or an exertion force applied to the lid member 412, the cartridge 310 directly, or both as a unitary member, can cause the fragrance cartridge 310 to contact the rupture device 115. As such, a rupturable seal disposed on a bottom of the cartridge 310 can be compromised to release the contents of the cartridge into the base member 114. In the embodiment of FIG. 3B, the cartridge 310 has a disc structure configuration instead of a tubular configuration as shown in FIGS. 1-3A. It is noted that the cartridge can be any suitable shape that can cooperate with and complement the absorbent member and rupture device. The fragrance medium contained within the cartridge and released into the base member can be absorbed by the absorbent member 210. The fragrance medium can permeate evenly throughout the absorbent member 210 and the fragrance can emanate from the absorbent member to the surrounding external environment via wicking transference.

As depicted in FIGS. 1-5, the absorbent member 210 can be a monolithic unit such that the fragrance medium of a cartridge 310 can be absorbed by the entire absorbent member 210. In other embodiments (not shown), the absorbent member can be segmented with a nonabsorbent dividing material and the corresponding reservoir basin can also be segmented with a divider or by configuration. This can allow a fragrance medium to be deposited in a segmented portion of the reservoir basin to allow select portions of the absorbent member to absorb a fragrance medium. This construction may be used with a housing 110 having one aperture 113 therein, or more practically be used with a housing 110 having a plurality of apertures 113 such, as the embodiment of FIGS. 4-5.

The absorbent member 210 can be used more than once. Therefore, once the volatile components of the fragrance from the first fragrance cartridge have evaporated from the absorbent member, a second cartridge with the same scent can be utilized with the same absorbent member 210 to replenish the scent. Alternatively, a different fragrance can be utilized in the second cartridge, such as one that is complimentary with the first fragrance, while the original absorbent member 210 remains unchanged.

In the embodiments of FIGS. 1-5, the housing 110 and the absorbent member 210 are substantially circular in shape. However, the housing 110 and the absorbent member 210 can have any suitable shape such as for purposes of example, but not limited to, elliptical, square, rectangular, trapezoidal, round, cube, and the like. The housing 110 can further include shapes to resemble animals, fruits, letters, numbers, seashells, people, and other objects readily enjoyed by consumers.

Although the cartridge 310 is shown as circular or tubular in FIGS. 1-5, the cartridge 310 can be any suitable shape or configuration that complements the aperture 113 of the top member 112 or that complements the aperture of the absorbent member. Examples include, but not limited to, elliptical, square, rectangular, trapezoidal, round, cube, and the like. The cartridge 310 can have a rupturable surface at the base of the cartridge, such as a heat sealable foil. Examples of suitable rupturable surfaces are disclosed in U.S. Pat. No. 8,695,891 assigned to Takasago International Corporation, the contents of which is incorporated herein by reference in its entirety. The rupturable surface can be ruptured by the rupture device 115, so that fragrance medium initially contained therein is releasable upon contact. The force required to compress the rupturable surface of the cartridge 310 with the rupture device 115 is minimal and can be equal to the compression force exerted by a single finger of the consumer. For purposes of example, the rupture device can be engaged with the cartridge with a travel distance of only approximately 0.2 inches to approximately 0.3 inches required in order tear the seal and to effectively cause the contents of the cartridge to be released.

Materials for the top face and the base of the cartridge include any suitable heat sealable foil. Other than the base of the cartridge, the cartridge is impermeable, which provides for more flexibility with the kinds of fragrance mediums available as discussed herein. As shown in FIG. 1, the cartridge 310 can furthermore include a flange 313 that is disposed in the lip portion 118 of the aperture 113, as previously discussed.

The fragrance medium contained in the cartridge 310 can be any suitable medium that emanates a volatile active. Examples of suitable mediums include all commercially available fragrances and compositions. However, other volatile mediums that might be suitable for use in the device described herein include medicants, decongestants, insect repellants and malodor counteractants. Fragrances available from Takasago International Corporation U.S.A. (Rockleigh, N.J.) are particularly preferred. Therefore, the disclosed subject matter contemplates a broad range of options which would be suitable for use in the present device contributing to a fulfilling experience for a consumer as compared to conventional devices, as previously detailed.

Malodor control compositions may be used with the fragrance medium, either alone or in combination with a fragrance composition. Accordingly, the fragrance medium may be used to neutralize and/or control odors, instead of, or in addition to, providing a hedonically pleasing odor to the surrounding air space. Use of malodor control compositions may find utility in bathroom and kitchen applications, and other areas in which malodors are likely to be present.

The device can also deliver insecticides or insect repellents. Insect repellents and insecticides known to those of ordinary skill in the art can be used. Preferred insect repellent compositions include insect repellent compositions containing para-menthane diol, commercially available from Takasago International Corporation U.S.A. (Rockleigh, N.J.).

The device of the present application may be applied to household rooms and used as an air freshener. Alternatively, the liquid-evaporative delivery device may be used in an office environment (e.g., at reception areas), or a place of business (e.g., checkout counter) or a place of recreation (e.g., a gym).

In accordance with the embodiments of the subject matter previously described, the components of the housing can be made out of a plurality of suitable materials. For instance, the materials can include plastic, thermoplastic, or thermoformed compositions such as, but not limited to, polypropylene, polyethylene, polyethylene terephthalate and the like. All of the materials offering the ability to be flexed in so some way so as to allow for the deflection of the cartridge contained in the top housing to be engaged with the rupture device.

In accordance with the embodiments of the subject matter previously described, the components of the absorbent member can be made out of a plurality of suitable materials. For instance, the suitable materials include porous polyethylene, ceramic, porcelain, terra cotta, paper, wood, nonwovens, felted fabrics, plaster of paris, and micro porous polyolefin (Teslin™), as well as various foams to include compositions based upon polyether, polyester and polyurethane chemistries.

While the disclosed subject matter is described herein in terms of certain preferred embodiments, those skilled in the art will recognize that various modifications and improvements can be made to the disclosed subject matter without departing from the scope thereof. Additional features known in the art likewise can be incorporated, such as disclosed in U.S. Pat. No. 8,695,891, entitled "Dual Functioning Fragrance Delivery Device," and owned by the Assignee of record, and U.S. Publication No. 2012/0312893, entitled "Volatile Medium Delivery Device," and owned by the Assignee of record, which are incorporated in their entirety by reference herein. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the various embodiments depicted and claimed, the disclosed subject matter is also directed to other embodiments having any other possible combination of the features disclosed and claimed herein. As such, the particular features presented herein can be combined with each other in other manners within the scope of the disclosed subject matter such that the disclosed subject matter includes any suitable combination of the features disclosed herein. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the device and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A fragrance delivery system, comprising:
a housing including a top surface movable between a first position and a second position and a rupture device;
an absorbent member receivable in the housing; and
a cartridge insertable within the housing and containing a fragrance medium therein, wherein the top surface includes a plurality of slits, wherein the slits increase the flexibility of the top surface and the top surface is deflectable towards the rupture device of the housing between the first position and the second position by exerting a downward force on the cartridge to deflect the top surface, wherein the rupture device of the housing engages with the cartridge when the top surface is in the second position to release the fragrance medium from the cartridge into the housing, and wherein the absorbent member absorbs the fragrance medium and permeates a fragrance from the fragrance medium to an external environment.

2. The fragrance delivery system of claim 1, wherein the housing includes a base member comprising the rupture device and a top member which includes the top surface.

3. The fragrance delivery system of claim 2, wherein the top surface of the top member includes at least one sidewall depending therefrom.

4. The fragrance delivery system of claim 2, wherein the top member defines at least one aperture that receives the cartridge therein.

5. The fragrance delivery system of claim 2, wherein the top member further defines a second aperture therein and the fragrance delivery system further comprises a second cartridge containing a fragrance medium therein and receivable within the second aperture of the top member.

6. The fragrance delivery system according to claim 5, wherein the top member is rotatable with respect to the base member and the second cartridge is engageable with the rupture device of the base member to release the fragrance medium from the second cartridge.

7. The fragrance delivery system of claim 2, wherein the base member includes at least one support.

8. The fragrance delivery system of claim 2, wherein the base member includes a convex configuration and channels fragrance medium released from the cartridge away from a center of the base member towards a contact surface of the absorbent member.

9. The fragrance delivery system of claim 1, wherein the absorbent member defines an aperture therein and comprises at least one of cylindrical or disc configuration, wherein the rupture device is receivable within the aperture of the absorbent member.

10. The fragrance delivery system of claim 1, wherein the cartridge comprises a rupturable seal at a bottom thereof.

11. The fragrance delivery system of claim 1, wherein the fragrance medium comprises an insecticide.

12. The fragrance delivery system according to claim 1, wherein the cartridge comprises at least 8 grams of fragrance medium.

13. The fragrance delivery system according to claim 1, wherein the absorbent member diffuses the fragrance medium to an external environment for at least 28 days.

14. The fragrance delivery system according to claim 1, wherein the fragrance medium includes a colorant and the absorbent member absorbs color of the colorant.

15. The fragrance delivery system of claim 1, further comprising a lid member engageable with the housing, wherein the cartridge is coupled to the lid member.

16. The fragrance delivery system of claim 15, wherein the lid member is compressible with respect to the base member to engage the cartridge with the rupture device.

17. A fragrance delivery device, comprising:
a housing including a top surface movable between a first position and a second position, at least one sidewall coupled to the top surface, and a base member including a rupture device, wherein the top surface defines an aperture therein;
an absorbent member disposed within the housing, wherein the base member supports the absorbent member; and
a cartridge insertable within the aperture of the top surface and containing a fragrance medium therein, wherein the top surface includes a plurality of slits, wherein the slits increase the flexibility of the top surface and the top surface is deflectable towards the base member between the first position and the second position by exerting a downward force on the cartridge to deflect the top surface to engage a bottom of the cartridge with the rupture device to release the fragrance medium from the cartridge into the base member when the top surface is in the second position, and wherein the absorbent member absorbs the fragrance medium and permeates a fragrance from the fragrance medium to an external environment.

18. A method of operating a fragrance delivery system, comprising:
providing a fragrance delivery device including
a housing including a rupture device and a top surface movable between a first position and a second position, wherein the top surface includes a plurality of slits, wherein the slits increase the flexibility of the top surface, and an absorbent member receivable in the housing;
inserting a cartridge within the housing, wherein the cartridge contains a fragrance medium therein;
engaging the cartridge with the rupture device of the housing by exerting a downward force on the cartridge to deflect the top surface from the first position towards the rupture device of the housing to release the fragrance medium from the cartridge into the housing when the top surface is in the second position, wherein the absorbent member absorbs the fragrance medium and permeates a fragrance from the fragrance medium to an external environment.

19. The method of claim 18, wherein exerting the downward force on the cartridge transitions the cartridge between an initial position above the rupture device to a second position engaged with the rupture device.

20. The fragrance delivery system of claim 4, wherein the top member further defines a lip portion about the aperture that corresponds with a flange of the cartridge, that engages the lip portion to deflect the top surface between the first position and the second position.

21. The fragrance delivery system of claim 1, wherein the top surface deflects back to the first position after the rupture device of the housing engages with the cartridge.

* * * * *